United States Patent [19]

Weeks

[11] Plant 4,558

[45] Jul. 1, 1980

[54] ROSE PLANT

[76] Inventor: O. L. Weeks, 926 W. Philadelphia, Ontario, Calif. 91761

[21] Appl. No.: 3,816

[22] Filed: Jan. 15, 1979

Related U.S. Application Data

[63] Continuation of Ser. No. 845,240, Oct. 25, 1977, abandoned.

[51] Int. Cl.[2] ..... A01H 5/00

[52] U.S. Cl. ..... Plt./17

[58] Field of Search ..... Plt./17

*Primary Examiner*—Robert E. Bagwill
*Assistant Examiner*—James R. Feyrer
*Attorney, Agent, or Firm*—Frank B. Robb

[57] ABSTRACT

There is disclosed a new variety of rose plant, particularly distinguished by its unusual range of color change from light yellowish pink to dark reddish orange of newer flowers to a moderate pink to deep pink and dark reddish orange as the blooms weather and age, a frosty white overlay also then appearing, rather short, full buds with many petals, long strong stems for cut flowers with thick waxy foliage leaflets.

4 Drawing Figures

This application is a continuation of application Ser. No. 845,240 filed Oct. 25, 1977 now abandoned.

DESCRIPTION OF THE INVENTION

The present invention relates to a new and distinct variety of rose plant of the hybrid tea class, which was originated by me in a breeding program which I carry on continuously and as a result involves many complex crosses generally, the instant variety of this invention being the result of crossing a seedling of the variety "First Prize", U.S. Plant Pat. No. 2,774, the seed parent hereof, with an unnamed seedling, which is identified in my records as 6742-A-33, the pollen parent, my new variety itself being identified by me as 76-R-10.

The variety which I have produced and is herein described, is new and improved, being distinguished from its parents and from all other rose varieties of which I have knowledge, as evidenced by the following unique combination of principal characteristics which are outstanding in the said new variety:

(1) Distinctive light yellowish pink to dark reddish orange coloring of the blooms which age to moderate to deep pink and dark reddish orange with white overlay;

(2) Shorter, fuller buds;

(3) Larger, more formal flowers;

(4) Reduced legginess and more closed formation of the canes;

(5) Fewer thorns; and (6) Heavier, more waxy foliage leaflets.

Comparison of my new variety with the seed parent "First Prize" emphasizes the decidedly more orangey-pink color of the new blooms, whereas those of "First Prize" are of more pink shadings with more reddish overlay, which develops as aging progresses, whereas my new variety retains its reddish orange while a frosty white overlay appears as aging continues.

The pollen parent 6742-A-33, of my breeding, is a complex result of crosses of "Happiness" U.S. Plant Pat. No. 911, "Chrysler Imperial" U.S. Plant Pat. No. 1,167, and "El Capitan" U.S. Plant Pat. No. 1,796, thereby producing in said unnamed seedling a definite red coloring with flowers of considerably smaller size with less formal shape than my new variety. The foliage leaflets of my new variety are heavier and more waxy than those of this pollen parent.

Asexual reproduction of my new variety by budding performed by me at Chino, Calif., shows the aforementioned characteristics and distinctions come true to form, are established and transmitted through succeeding generations and propagation.

The accompanying drawing shows typical specimens of the vegetative growth and flowers of my new variety in different stages of development, and as depicted in color as nearly true as it is reasonably possible to make the same in a color illustration of this character.

Further the following detailed description of my new variety, with color terminology in accordance with Nickerson Color Fan, published by Munsell Color Company of Baltimore, Md., except where general color terms of ordinary dictionary significance are appropriate the observations having been made using incandescent daylight bulb lighting:

Type: Hardy; tall; bush; greenhouse and outdoors; for cut flowers and garden decoration.

Class: Hybrid tea.

Breeding: Seedling.

*Seed parent.*—"First Prize" U.S. Plant Pat. No. 2,774.

*Pollen parent.*—An unnamed seedling identified as 6742-A-33 in my records.

Propagation: Holds its distinguishing characteristics through successive propagations by budding.

FLOWERS

Locality where grown and observed: Ontario and Chino, Calif.

Flowers borne: Usually 3 to a stem, in irregular rounded pyramidal clusters; on normally strong medium length stems.

Quantity of bloom: Abundant outdoors and in the greenhouse.

Continuity: From intermittent to continuous.

Fragrance: Virtually none.

Bud:

*Peduncle.*—Medium length; medium to heavy caliper; erect; green bronze; medium rough; numerous brown prickles. Color — green bronze.

*Before calyx breaks.*—Size — large. Form — medium length; oval; with a conspicuous neck; with foliaceous appendages on the surface of the bud; with stout much cut foliaceous parts extending beyond the tip of the bud equal to ¼ or more of its length. Color — yellowish green with some bronze at tips.

*As calyx breaks.*—Color — yellowish green with cut edges a bronze color.

*As petals first open.*—Size — from medium to large. Form — short to long and ovoid. Color — outside — near a dark reddish orange 7.5R4/11 but lighter with a few highlights of strong yellowish pink 7.5R7/9. Inside — petal a blend of strong reddish orange 7.5R6/12 and a strong reddish orange 7.5R5/13 and a dark reddish orange 7.5R4/11. Opening — opens up well.

Bloom:

*Size (when fully open).*—Large from 4 inches to 4½ inches.

*Petalage.*—Double; from 20 to 25 petals.

*Form.*—Full, high centered and ovoid at first; becoming cupped and high centered; petals being at first very tightly rolled outward; becoming later at maturity, very loosely rolled outward and flat.

Petals:

*Texture.*—Thin and soft with inside shiny.

*Appearance.*—Inside shiny; outside satiny.

*Shape.*—Outside — orbicular; scalloped; with flat apex with 3 notches. Intermediate — obovate; scalloped with apex flat with 1 to 2 notches. Inside — obovate; scalloped with apex flat with 1 notch.

This description of a newly opened flower was made from a rose grown outdoors at Ontario, Calif.:

*Color.*—Outer petal — outside surface — blending up into a blend of light yellowish pink 7.5R9/3 and a combination of moderate yellowish pink 7.5R8/6 and a strong yellowish pink 7.5R7/9. Inside surface — blending upward of light yellowish pink 7.5R9/3 into a moderate pink 5R8/6 but shades of near to a deep yellowish pink 5R6/11 and strong yellowish pink 5R7/9. Intermediate petal — outside surface — petal is essentially a strong reddish orange 7.5R6/12 but lighter and darker than a moderate yellowish pink 7.5R8/6. Inside surface — body of petal is near a blend but lighter than vivid red 5R5/13 and darker than a deep yellowish pink 5R6/11 blending upward to a strong yellowish pink 5R7/9 with veins near a vivid red 5R5/13. Inner petal — outside surface — petal is a blend of a dark reddish orange 7.5R4/11 and near shades of strong yellowish pink 7.5R7/9 and strong reddish orange 7.5R/13. Inside surface — petal blends from near a dark reddish orange 7.5R4/11 with a minute top margin of a moderate pink 5R8/6 but lighter.

The following description was made from a rose plant that was opened for three days outdoors at Ontario, Calif.:

*Color.*—Outer petal — outside surface — petal is between a strong yellowish pink 7.5R7/9 but lighter and darker than a moderate yellowish pink 7.5R8/6. Inside surface — petal is between a deep yellowish pink 5R6/11 and a deep pink 2.5R6/11 blending upward to a moderate pink 2.5R8/5 but a little lighter. Inner petal — outside surface — between a strong yellowish pink 5R7/9 and a strong yellowish pink 7.5R7/9 but lighter. Inside surface — petal is near a strong pink 2.5R7/8 with veins a deep pink 2.5R6/11. General color effect — newly opened flower — a blend of light yellowish pink 7.5R9/3 and dark reddish orange 7.5R4/11. 3-days open — a variance between moderate pink 5R8/6 deep pink 2.5R6/11 and dark reddish orange 7.5R4/11.

*Behavior.*—Drop off cleanly.

*Flower longevity.*—On bush in garden — 3 to 4 days in October. Cut roses grown outdoors kept at living room temperatures 3 to 4 days in October.

REPRODUCTIVE ORGANS

Stamens: Many; arranged regularly about pistils, mixed with petaloids, tucked in calyx.

Filaments: Short to medium length; most with anthers.

*Color.*—Reddish.

Anthers: Medium to large size; all open at once.

*Color.*—Yellow.

Pollen: Abundant.

*Color.*—Gold yellow.

Pistils: Many.

Styles: Uneven; short to medium length; medium caliper; bunched.

Stigma:

*Color.*—Pinkish.

Ovaries: All enclosed in calyx.

Hips: None observed.

Sepals: Permanent; very long; spear-shaped; recurved.

*Color.*—Light green with gray streak up center.

Seeds: None observed.

PLANT

Foliage:

*Leaves.*—Compound of 3–7 leaflets; normal to abundant; medium to large size; heavy, leathery and wrinkled.

*Leaflets.*—Shape — ovate with apex obtuse; base round; margin irregularly serrate.

*Color.*—Mature — upper surface — green. Under surface — very dark bronze. Young — upper surface — very dark bronze. Under surface — reddish bronze.

*Rachis (the supporting stem of the compound leaf).*—Light to medium weight. Upper side — smooth; grooved. Under side — somewhat thorny.

*Stipules.*—Medium length; medium width; medium long points; turning out at an angle of less than 45 degrees.

*Disease and insect resistance.*—Average resistance to powdery mildew.

Growth:

*Habit.*—Bushy; upright; much branched.

*Growth.*—Very vigorous.

*Canes.*—Medium caliper.

*Main stems.*—Color — dull green. Large prickles — several; medium long; hooked downward; with long narrow base. Color — brown. Small prickles — few. Color — brown. Hairs — none.

*Branches.*—Color — yellowish green. Large prickles — several; medium length; hooked downward with long narrow base. Color — yellowish green. Small prickles — none. Hair — none.

*New shoots.*—Color — bright bronze. Large prickles — medium, long; hooked downward with long narrow base. Color — bronze with yellow tips. Small prickles — none. Hairs — none.

I claim:

1. A new and distinct variety of rose plant of the hybrid tea class, substantially as herein shown and described, characterized particularly as to novelty by the unique combination of a distinctly orangey-pink coloring of mature blooms which change to reddish orange as the blooms age, a white overlay appearing as the blooms age, a shorter fuller bud than the present "First Prize", the flowers being larger and more formal with medium length, strong stems, relatively few thorns and heavy, waxy foliage.

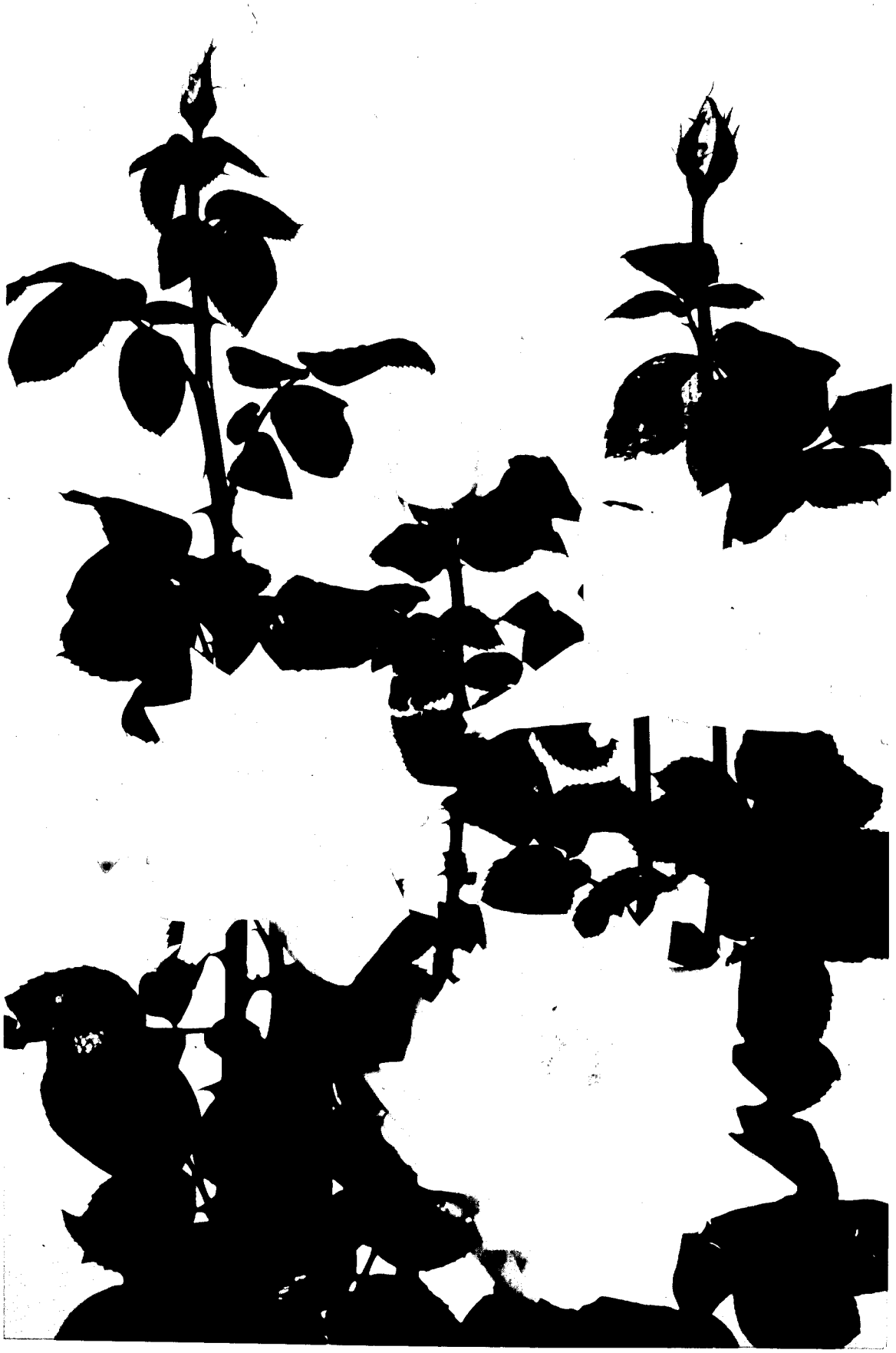

* * * * *